US00PP27093P2

(12) United States Plant Patent
Hartman

(10) Patent No.: US PP27,093 P2
(45) Date of Patent: Aug. 23, 2016

(54) ***CALADIUM* PLANT NAMED 'CLASSIC PINK'**

(50) Latin Name: *Caladium×hortulanum*
Varietal Denomination: Classic Pink

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 105 days.

(21) Appl. No.: 14/544,176

(22) Filed: Dec. 4, 2014

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — June Hwu
(74) *Attorney, Agent, or Firm* — C. A. Whealy

(57) ABSTRACT

A new and distinct cultivar of *Caladium* plant named 'Classic Pink', characterized by its intermediate height, upright and uniformly mounded plant habit; vigorous growth habit and rapid growth rate; fancy-type leaves that are deep rose pink in color surrounded by dark green-colored margins; and good landscape performance.

4 Drawing Sheets

Botanical designation: *Caladium×hortulanum.*
Cultivar denomination: 'CLASSIC PINK'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Classic Pink'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2009 in Avon Park, Fla. of a proprietary selection of *Caladium×hortulanum* identified as code number WS-03-36, not patented, as the female, or seed, parent with *Caladium×hortulanum* 'Red Flash', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2010.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2011 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Classic Pink'. These characteristics in combination distinguish 'Classic Pink' as a new and distinct *Caladium* plant:

1. Intermediate in height, upright and uniformly mounded plant habit.
2. Vigorous growth habit and rapid growth rate.
3. Fancy-type leaves that are deep rose pink in color surrounded by dark green-colored margins.
4. Good landscape performance.

Plants of the new *Caladium* differ primarily from plants of the female parent selection in the following characteristics:

1. Plants of the new *Caladium* are faster growing and produce finished plants about one week earlier than plants of the female parent selection.
2. Plants of the new *Caladium* and the female parent selection differ in leaf shape and color as leaves of plants of the female patent selection are lance leaf-types that are dark green in color with grey green-colored centers occasionally blushed with pink.
3. Plants of the new *Caladium* and the female parent selection differ in leaf petiole color as leaf petioles of plants of the female patent selection are tan pink in color with darker-colored stippling and tessellations.

Plants of the new *Caladium* differ primarily from plants of the male parent, 'Red Flash', in the following characteristics:

1. Plants of the new *Caladium* are shorter than plants of 'Red Flash'.
2. Plants of the new *Caladium* are faster growing and produce finished plants about one week earlier than plants of 'Red Flash'.
3. Plants of the new *Caladium* and 'Red Flash' differ in leaf color as leaves of plants of 'Red Flash' are dark green in color with dark red-colored centers and primary veins and pink-colored spots.

Plants of the new *Caladium* can be compared to plants of *Caladium×hortulanum* 'Rosebud', not patented. In side-by-side comparisons, plants of the new *Caladium* differed primarily from plants of 'Rosebud' in the following characteristics:

1. Plants of the new *Caladium* were taller and more vigorous than plants of 'Rosebud'.
2. Plants of the new *Caladium* and 'Rosebud' differed in leaf color as leaves of plants of 'Rosebud' had light to pale pink-colored centers surrounded by a broad area of white-colored speckling and green-colored margins.
3. Plants of the new *Caladium* and 'Rosebud' differed in leaf petiole color as leaf petioles of plants of 'Rosebud' were green and tan in color with darker-colored stippling and tessellations.
4. Plants of the new *Caladium* were more tolerant to *Pythium* Root Rot than plants of 'Rosebud'.

Plants of the new *Caladium* can also be compared to plants of *Caladium×hortulanum* 'Rose Glow', disclosed in U.S. Plant Pat. No. 20,070. In side-by-side comparisons, plants of the new *Caladium* differed primarily from plants of 'Rose Glow' in the following characteristics:

1. Plants of the new *Caladium* were more vigorous than plants of 'Rose Glow'.
2. Plants of the new *Caladium* and 'Rose Glow' differed in leaf color as leaves of plants of 'Rose Glow' had pink-colored centers surrounded by a broad area of pink and white-colored speckling and green-colored margins.
3. Plants of the new *Caladium* and 'Rose Glow' differed in leaf petiole color as leaf petioles of plants of 'Rose Glow' were tan green in color with dark-colored tessellations and speckling.
4. Plants of the new *Caladium* were more tolerant to *Pythium* Root Rot than plants of 'Rose Glow'.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Classic Pink' in a container and grown in a shadehouse (tuber not de-eyed).

The photograph at the top of the second sheet is a comparison view of typical potted plants of the male parent, 'Red Flash' (left), 'Classic Pink' (center) and the female parent selection (right).

The photograph at the bottom of the second sheet is a comparison view of typical potted plants of 'Rosebud' (left), 'Classic Pink' (center) and 'Rose Glow' (right).

The photograph at the top of the third sheet is a comparison view of typical plants of 'Classic Pink' grown in containers; the plant on the right has not had its tuber de-eyed and the plant on the left has had its tuber de-eyed prior to planting.

The photograph at the bottom of the third sheet is a close-up view of typical freshly-harvested tubers and roots of 'Classic Pink'.

The photograph at the top of the fourth sheet is a side perspective view of typical plants of 'Classic Pink' grown in an open field.

The photograph at the bottom of the fourth sheet is a close-up view of a typical inflorescence of 'Classic Pink'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were eight weeks old, and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Classic Pink'.

Parentage:

*Female, or seed, parent.*—Proprietary selection of *Caladium×hortulanum* identified as code number WS-03-36, not patented.

*Male, or pollen, parent.*—*Caladium×hortulanum* 'Red Flash', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and somewhat flattened; individual segments elliptic to ovate in shape. Height: About 3.4 cm. Diameter: About 4.2 cm to 5.5 cm. Segment height: About 2.6 cm to 3.1 cm. Segment diameter: About 2.5 cm to 3.9 cm. Texture: Thick, starchy; somewhat brittle. Color: Epidermis, freshly-harvested: Close to 199A to 199B. Epidermis, dried: Close to 200A. Cortical tissue: Close to 2C to 2D. Axillary buds: Close to 155C and 36C. Root description: Thick, fleshy contractile roots; color, close to 155C and 199C. Rooting habit: Sparse to medium density.

Plant description:

*Plant type.*—Herbaceous perennial; suitable as a potted plant in containers 15-cm to 25-cm and suitable as a landscape plant in shaded areas.

*Plant and growth habit.*—Intermediate in height, upright and uniformly mounded plant habit; vigorous and dense growth habit; rapid growth rate, potted plants in finished or saleable form in about eight weeks after planting tubers; leaf petioles and leaves arise from one or more growing points on tubers; petioles mostly upright and leaning outwardly with development.

*Plant height, from soil level to top of foliar plane, shadehouse-grown potted plants.*—About 29 cm to 32 cm.

*Plant height, from soil level to top of inflorescences, shadehouse-grown potted plants.*—About 32.5 cm.

*Plant diameter or spread, shadehouse-grown potted plants.*—About 39 cm to 42 cm.

*Number of shoots per plant, shadehouse-grown potted plants, tubers not de-eyed*.—About three to four develop per #1 tuber.

*Number of shoots per plant, shadehouse-grown potted plants, tubers de-eyed*.—About four to six develop per #1 tuber.

*Cataphylls, shadehouse-grown potted plants*.—Length: About 5.3 cm to 9 cm. Width: About 1 cm to 1.8 cm. Shape: Wedge-shaped. Apex: Acute or cuspidate. Base: Sheathing the stem. Color, inner surface: Close to N155B; colors and patterns of the outside surface are visible on the inner surface. Color, outer surface: Close to N155C and N170D tinged with close to 182C to 182D; densely and variably streaked and stippled with close to 200A tinged with close to 147A; with development, color becoming closer to 199A to 199B stained with close to 187A.

Leaf description:

*Arrangement and type*.—Alternate; simple; fancy-type.

*Length, shadehouse-grown potted plants*.—About 15 cm to 24 cm.

*Width, shadehouse-grown potted plants, flattened*.—About 10 cm to 18 cm.

*Shape*.—Broadly ovate.

*Apex*.—Acuminate to acute.

*Base*.—Sagittate to peltate.

*Margin*.—Entire; mostly flat with broad undulations.

*Texture, upper and lower surfaces*.—Smooth, glabrous.

*Luster, upper surface*.—Dull sheen.

*Luster, lower surface*.—Glaucous, dull sheen.

*Venation pattern*.—Pinnate.

*Color, shadehouse-grown potted plants*.—Developing leaves, upper surface: Main colors: Center, close to 184B tinged with close to 53B and 184A; towards the margins, close to 147A. Margins: Close to 147A. Basal notch: Close to 187A. Midrib and primary venation: Close to 185A tinged with close to 53A; random areas adjacent to venation, close to 194B, 147A and 182B. Developing leaves, lower surface: Main colors: Center, close to 184D; towards the margins, close to 191A. Margins: Close to 187A. Basal notch: Close to 187A. Midrib: Close to 184B; areas adjacent to venation, close to 159D tinged with close to 182D. Primary venation: Close to 184C; areas adjacent to venation, close to 159D tinged with close to 182D. Fully expanded leaves, upper surface: Main colors: Center, close to 53B; towards the margins, close to darker and greener than 147A tinged with close to N189A. Margins: Close to darker and greener than 147A tinged with close to N189A. Basal notch: Close to 187A. Midrib and primary venation: Close to 53A; random areas adjacent to venation, close to between 183A and 185A. Fully expanded leaves, lower surface: Main colors: Center, close to 184C; towards the margins, close to 191A. Margins: Close to 187A. Basal notch: Close to 187A. Midrib: Close to between 184B and 53B; areas adjacent to venation, close to 159D and 182D. Primary venation: Close to 184B; areas adjacent to venation, close to 159D and 182D.

*Petioles*.—Aspect: Initially upright and straight; with development, leaning outwardly; flexible. Length, shadehouse-grown potted plants: About 22.5 cm to 26.5 cm. Diameter, distal, shadehouse-grown potted plants: About 3.5 mm to 4.5 mm. Diameter, proximal, shadehouse-grown potted plants: About 8 mm to 10 mm. Texture: Smooth, glabrous; glaucous. Color, shadehouse-grown potted plants, Just below the leaf and petiole junction: Close to 184B. Overall: Close to 184C to 184D, boldly striped with close to 200A to 200B. Wing length, shadehouse-grown potted plants: About 5 cm to 6.8 cm. Wing diameter, shadehouse-grown potted plants: About 6 mm to 11 mm. Texture, inner and outer surfaces: Smooth, glabrous. Wing color, shadehouse-grown potted plants, inner surface: Close to N155A. Wing color, shadehouse-grown potted plants, outer surface: Close to N155C and N170D tinged with close to 181D, and densely and variably streaked and stippled or mottled and striped with close to 200A tinged with close to 147B.

Inflorescence description: Inflorescences observed on 7.5 week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet, jasmine-like with camphor note.

*Natural flowering season and flower longevity*.—Plants of the new *Caladium* typically flower during the spring in central Florida; early flowering habit, flowers develop about 7.5 weeks after growth commences; inflorescences last about three days before fading; inflorescences persistent.

*Spathe*.—Length, overall: About 12 cm. Length, distal open portion: About 8 cm. Length, proximal closed portion: About 4 cm. Width, distal open portion: About 5.3 cm. Width, at constriction: About 1.5 cm. Width, proximal closed portion: About 3.2 cm. Shape: Ovate to elliptic. Apex: Acuminate. Base: Obtuse. Margin: Entire. Texture, front and rear surfaces: Smooth, glabrous. Luster, front surface: Dull sheen. Luster, rear surface: Glaucous. Color, front surface: Distal open portion: Close to N155D tinged with close to 192D and 181D; with development, color becoming closer to 199B. Proximal closed portion: Close to 194B; towards the base, tinged with close to 187A to 187B and N186C; color does not change with development. Color, rear surface: Distal open portion: Close to N155D and N170D tinged and streaked with close to 146D; color does not change with development. Proximal closed portion: Close to 185A to 185B and 182B to 182C with variable areas close to 147B to 147C; color does not change with development.

*Spadix*.—Length: About 7.4 cm. Length, male flower zone: About 3.6 cm. Length, sterile zone: About 1.7 cm. Length, female flower zone: About 2.1 cm. Diameter, male flower zone: About 9 mm. Diameter, sterile flower zone: About 5 mm. Diameter, female flower zone: About 9 mm. Shape: Columnar. Apex: Obtuse. Base: Obtuse. Aspect: Upright. Color, mature, male zone: Close to 159D. Color, mature, sterile zone: Close to 159C. Color, mature, female zone: Close to 36D and 182D. Male flowers: Quantity per spadix: About 135. Shape: Obovate. Height: About 3 mm. Diameter: About 3 mm. Pollen amount: Moderate. Pollen color: Close to 4C. Female flowers: Quantity per spadix: About 119. Shape: Obovate. Height: About 3 mm. Diameter: About 1.5 mm. Stigma color: Close to 36D. Ovary color: Close to 182D and 155C.

*Scape*.—Length: About 20.5 cm. Diameter: About 7 mm. Strength: Sturdy; flexible. Aspect: Mostly erect. Texture: Smooth, glabrous; glaucous. Color, just below spathe: Variable stripes, close to 184A, 184B, 183D, 194B and 200D. Color, overall: Stripes, close to 182C, 182D, N170D and 200D.

*Seeds and fruits*.—To date, seed and fruit development have not been observed on plants of the new *Caladium*.

Disease & pest tolerance: Plants of the new *Caladium* have been observed to have above average tolerance to *Pythium* Root Rot and *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Classic Pink' as illustrated and described.

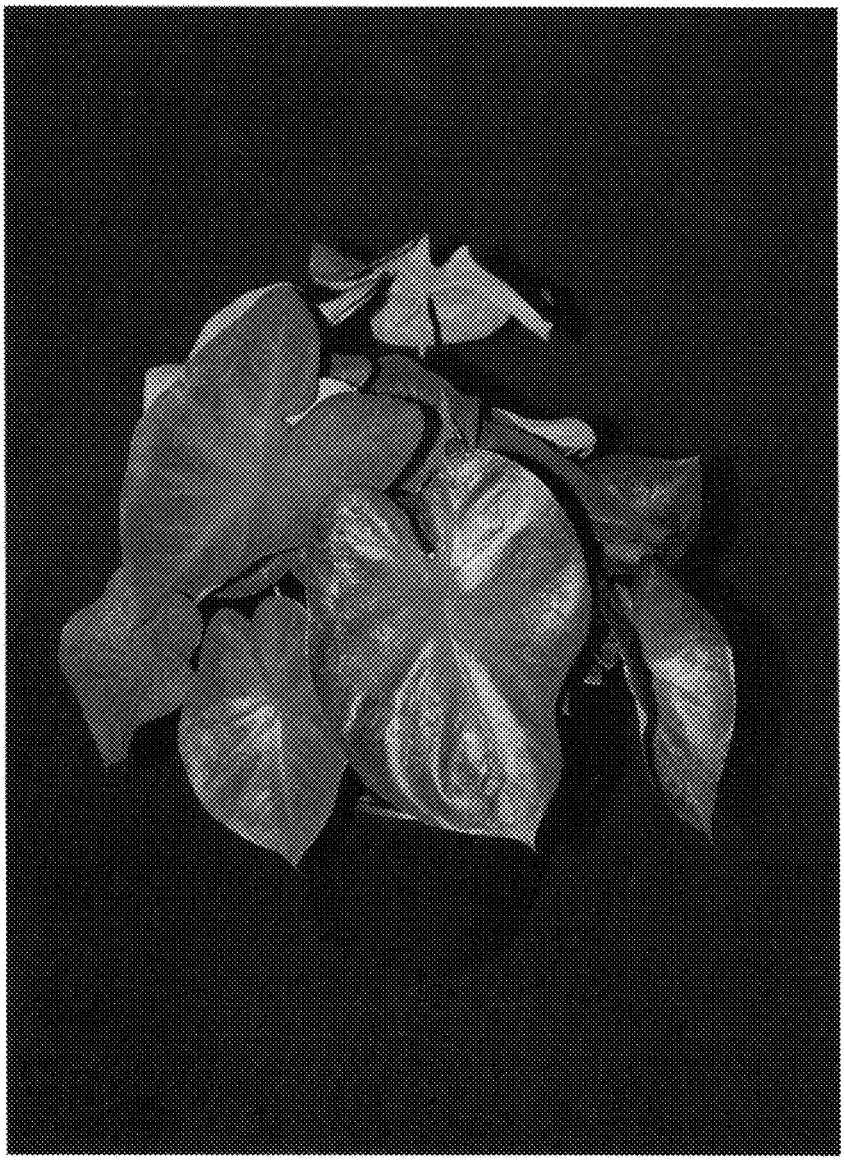

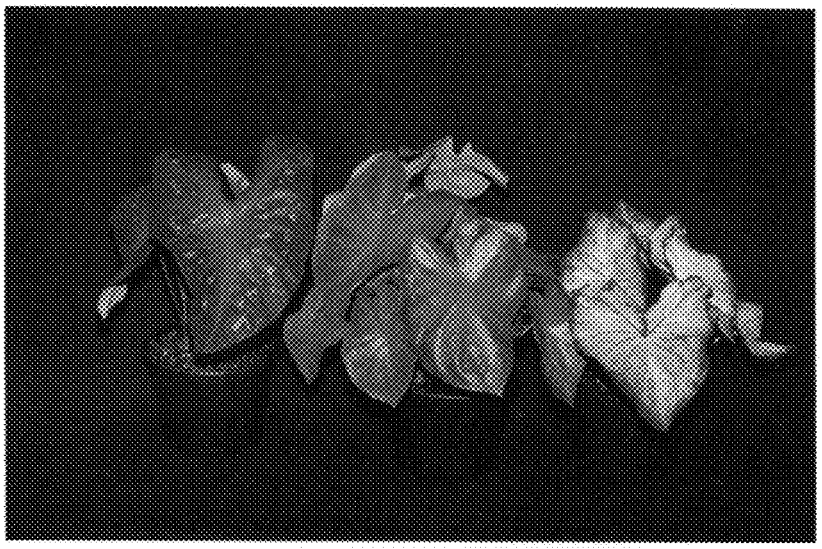
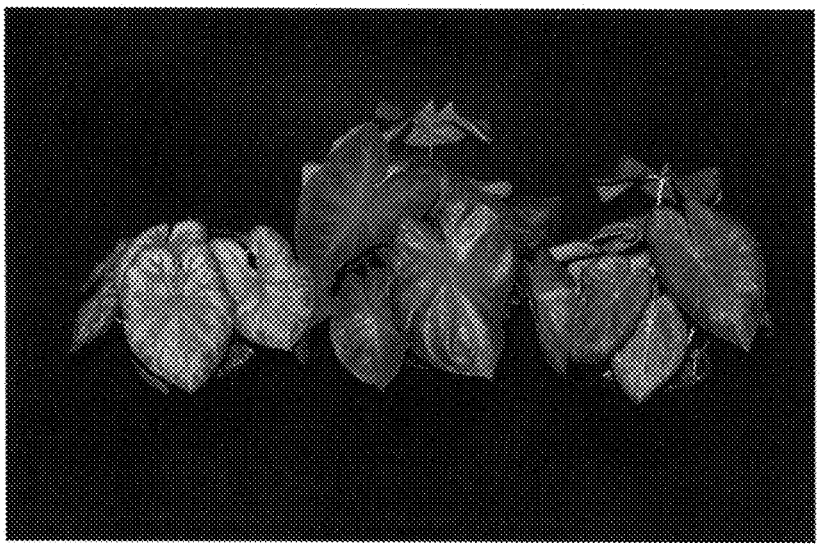

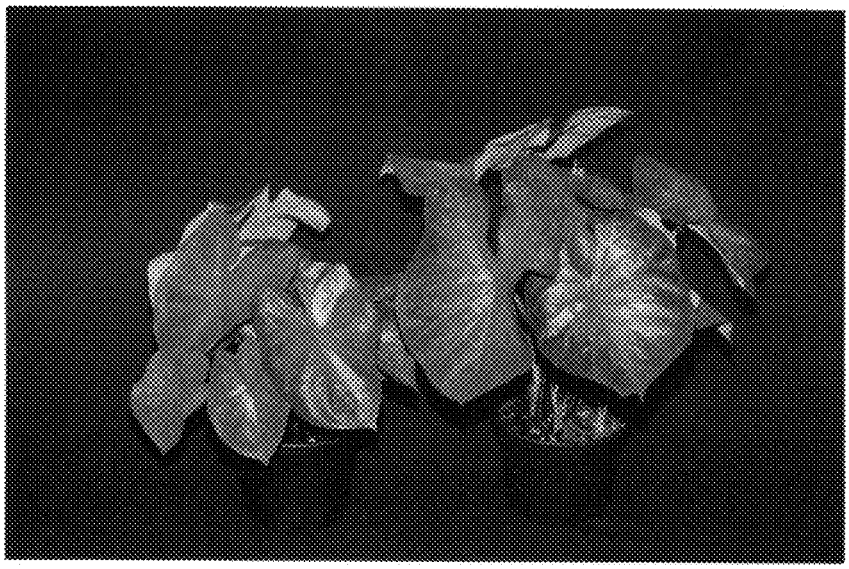
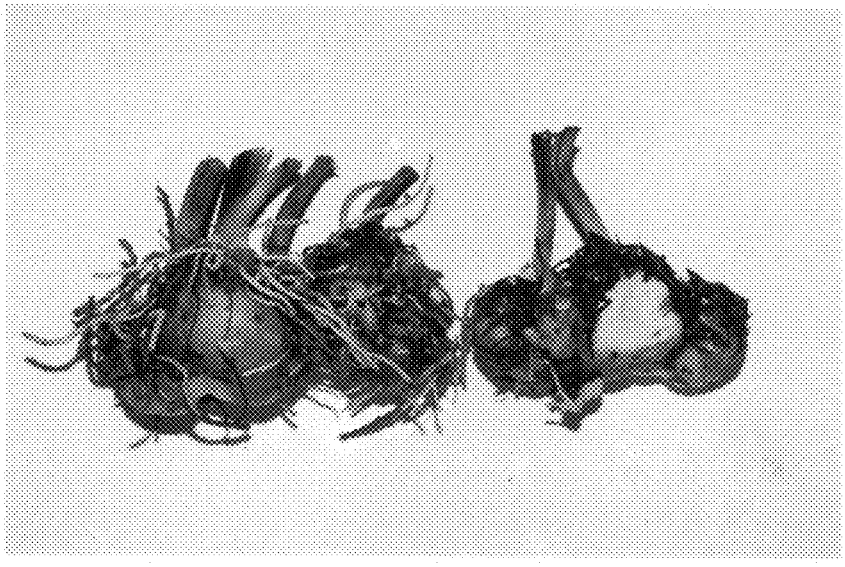

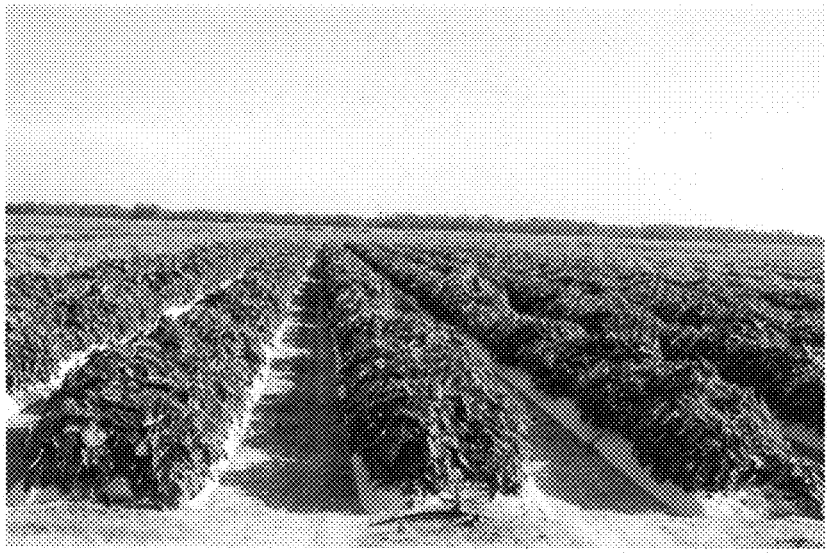
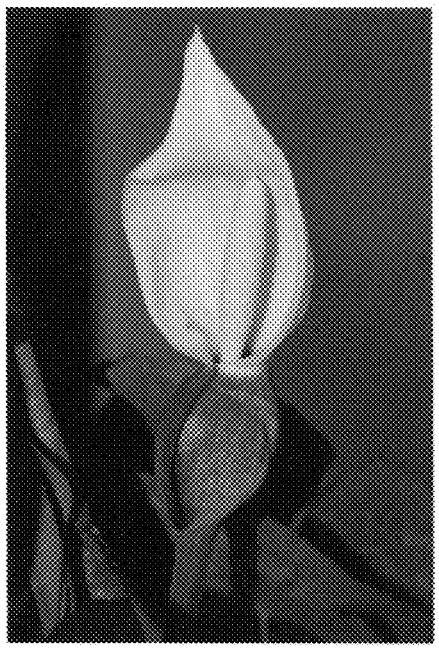

* * * * *